(12) United States Patent
Bertozzi et al.

(10) Patent No.: US 8,149,988 B2
(45) Date of Patent: *Apr. 3, 2012

(54) USE OF NEARLY MONOCHROMATIC AND TUNABLE PHOTON SOURCES WITH NUCLEAR RESONANCE FLUORESCENCE IN NON-INTRUSIVE INSPECTION OF CONTAINERS FOR MATERIAL DETECTION AND IMAGING

(75) Inventors: William Bertozzi, Lexington, MA (US); Robert J. Ledoux, Harvard, MA (US)

(73) Assignee: Passport Systems, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/731,695

(22) Filed: Mar. 25, 2010

(65) Prior Publication Data

US 2011/0064200 A1    Mar. 17, 2011

Related U.S. Application Data

(63) Continuation of application No. 12/184,640, filed on Aug. 1, 2008, now Pat. No. 7,693,262, which is a continuation of application No. 11/358,969, filed on Feb. 22, 2006, now Pat. No. 7,409,042.

(60) Provisional application No. 60/655,043, filed on Feb. 22, 2005.

(51) Int. Cl.
*G01N 23/04* (2006.01)
*G01N 23/201* (2006.01)

(52) U.S. Cl. ................ 378/57; 378/88; 378/86
(58) Field of Classification Search .............. 378/6, 7, 378/70, 86–90
See application file for complete search history.

(56) References Cited

U.S. PATENT DOCUMENTS

| | | | |
|---|---|---|---|
| 3,496,357 A | 2/1970 | Putz Franz et al. | |
| 4,415,804 A | 11/1983 | Sowerby | |
| 4,446,568 A | 5/1984 | Williams et al. | |
| 4,788,704 A | 11/1988 | Donges et al. | |
| 4,941,162 A | 7/1990 | Vartsky et al. | |
| 4,980,901 A | 12/1990 | Miller | |
| 5,115,459 A * | 5/1992 | Bertozzi | 378/88 |
| 5,247,177 A | 9/1993 | Goldberg et al. | |
| 5,274,689 A | 12/1993 | Palathingal et al. | |
| 5,323,004 A | 6/1994 | Ettinger et al. | |

(Continued)

FOREIGN PATENT DOCUMENTS

JP     2004-219187 A     8/2004

(Continued)

OTHER PUBLICATIONS

Bertozzi, William, Poster: Material Identification and Object Imaging using Nuclear Resonance Fluorescence, Jul. 18, 2003, MIT, Dept. of Energy's Ofc of Nuclear Physics Workshop on the Role of the Nuclear Physics Research Community in Combating Terrorism.

(Continued)

*Primary Examiner* — Irakli Kiknadze
(74) *Attorney, Agent, or Firm* — Foley Hoag LLP (57) ABSTRACT

Methods and systems for detecting potential items of interest in target samples, using nuclear resonance fluorescence, utilize incident photon spectra that are narrower than traditional bremsstrahlung spectra but overlap nuclear resonances in elements of interest for purposes of detection, such as but not limited to the detection of threats in luggage or containers being scanned.

48 Claims, 10 Drawing Sheets

Schematic representation of Nuclear Resonance Fluorescence Scattering

U.S. PATENT DOCUMENTS

| | | | |
|---|---|---|---|
| 5,420,905 A * | 5/1995 | Bertozzi | 378/88 |
| 5,600,303 A | 2/1997 | Husseiny et al. | |
| 5,600,700 A | 2/1997 | Krug et al. | |
| 5,642,393 A | 6/1997 | Krug et al. | |
| 6,018,562 A | 1/2000 | Willson | |
| 6,088,423 A | 7/2000 | Krug et al. | |
| 6,108,396 A | 8/2000 | Bechwati et al. | |
| 6,175,117 B1 | 1/2001 | Komardin et al. | |
| 6,175,609 B1 | 1/2001 | Edic et al. | |
| 6,345,113 B1 | 2/2002 | Crawford et al. | |
| 6,376,267 B1 | 4/2002 | Noack et al. | |
| 6,442,233 B1 | 8/2002 | Grodzins et al. | |
| 7,242,747 B2 | 7/2007 | Zerle | |
| 2004/0109532 A1 | 6/2004 | Ford et al. | |
| 2005/0094765 A1 | 5/2005 | Bijjani et al. | |
| 2005/0111619 A1 | 5/2005 | Bijjani et al. | |

FOREIGN PATENT DOCUMENTS

| | | |
|---|---|---|
| WO | 9203722 A1 | 3/1992 |
| WO | 9203900 A1 | 3/1992 |
| WO | 99/39189 A2 | 8/1999 |

OTHER PUBLICATIONS

Degener et al., Dipole Excitations in 48Ti Studied by Nuclear Resonance Fluorescence, Nuclear Physics A513 (1990) 29-42.

Metzger, Electric Dipole Transitions from the 2.6 MeV Septuplet in Bi209, Physical Review 187 (1969) 1680-1682.

JPO Office Action, Japanese Patent Application JP2007-557117, Mar. 1, 2011.

Bertozzi, William & Ledoux, Robert; "Nuclear resonance fluorescence imaging in non-intrusive cargo inspection"; Nuclear Instruments & Methods in Physics Research, Secton-B:Beam Interactions With Materials and Atoms, Elsevier, vol. 241, No. 1-4, Dec. 1, 2005, pp. 820-825.

Supplementary European Search Report for application No. EP 06 84 9722, dated Aug. 30, 2011.

* cited by examiner

Figure 6: The spectrum of photons from the $^{19}$F(p, $\alpha\gamma$) reaction.

Figure 7

Figure 8. Effect of various filters on a bremsstrahlung spectrum.

Figure 9. Schematic representation of Nuclear Resonance Fluorescence Scattering

USE OF NEARLY MONOCHROMATIC AND TUNABLE PHOTON SOURCES WITH NUCLEAR RESONANCE FLUORESCENCE IN NON-INTRUSIVE INSPECTION OF CONTAINERS FOR MATERIAL DETECTION AND IMAGING

CROSS-REFERENCE TO RELATED APPLICATION

The present application claims the benefit of U.S. Utility patent application Ser. No. 12/184,640, which was filed Aug. 1, 2008, U.S. Utility patent application Ser. No. 11/358,969, which was filed Feb. 22, 2006, and U.S. Provisional Patent Application Ser. No. 60/655,043, entitled "Use Of Nearly Monochromatic And Tunable Photon Sources With Nuclear Resonance Fluorescence In Non-Intrusive Inspection Of Containers For Material Detection And Imaging," which was filed on Feb. 22, 2005 by William Bertozzi and Robert J. Ledoux, and are hereby incorporated by reference.

BACKGROUND OF THE INVENTION

1. Field of the Invention

This disclosure relates to non-intrusive scanning for materials (such as, for example, detection of explosives, nuclear materials, or contraband at airports, seaports, or other transportation terminals), and more particularly, to a method using nearly monochromatic and tunable photon sources with nuclear resonance fluorescence.

2. Background Information

Several factors may interfere with or limit the efficiency of the non-intrusive inspection of containers with Nuclear Resonance Fluorescence. In particular, non-intrusive inspection can be affected by phenomena that depend on the spectrum of photons used as the interrogating beam. Among others, these phenomena include: background noise that arises from photons in the beam that are non-resonant with any nuclear species of interest; background that arises from resonance fluorescence from nuclear species other than the species of interest present in the viewed voxel; radiation exposure that arises from photons in the beam that are non-resonant with nuclei of interest; and detector dead times due to non-resonant photons scattered by multiple processes. Therefore, the use of a photon beam with a limited range of photon energies can be advantageous over the use of a photon beam such as a bremsstrahlung beam. Some advantages associated with imaging with a narrower spectrum photon beam may include: increasing the speed of inspection; increasing the efficiency with which contraband is detected; decreasing the rate of false positive detection events; and/or decreasing the radiation dose delivered to the cargo volume.

The use of NRF measurements with some monochromatic energy sources has been demonstrated. For example, U.S. Pat. No. 5,040,200, Gamma-Gamma Resonance in Activation Analysis, and Particularly, its Application to Detection of Nitrogen Based Explosives in Luggage (Ettinger et al.), teaches scanning for a species of interest by using a sample of excited atoms of that species to generate photons that are resonant with nuclear transitions in that species of interest. A disadvantage of such sources is that they can only be used to scan for that single species of interest.

SUMMARY OF THE INVENTION

Methods and systems for detecting a potential item of interest in a target sample are described herein. In one aspect, the method comprises providing a source of photons with an energy spectrum that overlaps a nuclear resonance in the item of interest and is narrower than bremsstrahlung radiation; illuminating the target sample with photons from the source; providing at least one photon detector to measure an intensity of photons scattered from at least a portion the target sample in at least one energy channel; and identifying an item of interest detection event if the intensity of photons detected in at least one of the at least one energy channels of interest meets a predetermined item of interest detection criterion.

In some aspects, the method further comprises providing at least one reference scatterer, the reference scatterer comprising at least one nuclear species of interest; allowing photons transmitted through the target sample to scatter from the at least one reference scatterer; and providing at least one photon detector to measure an intensity of photons scattered from the at least one reference scatterer in at least one energy channel. The photon detector(s) which measure an intensity of photons scattered from the reference scatterer(s) may be in addition to or in place of the photon detector(s) which measure an intensity of photons scattered from the at least a portion of the target sample. An item of interest detection event may be identified if the intensity of photons detected in at least one of the at least one energy channels of interest measured by the photon detector(s) measuring reference scattering meets a predetermined item of interest detection criterion.

In some aspects, the source photons may be generated by the Compton scattering of photons by electrons. The source photon frequency may be tuned and the energy spectrum broadened from a monochromatic or nearly monochromatic photon line by an angular dependence of Compton scattered photon energy. The Compton scattering may be the backscattering of laser photons by energetic electrons. The laser photons may be free electron laser photons.

In some aspects, the source photons may be coherent bremsstrahlung photons generated by the passage of electrons through a periodic lattice.

In some aspects, the source photons may be generated by a particle-induced reaction in a nucleus. The nuclear decay following the particle-induced reaction may produce a two-body final state. The nuclear decay following the particle-induced reaction may produce a three-body final state. The particle-induced reaction may be neutron capture.

In some aspects, the source photons may be bremsstrahlung radiation photons passed through absorbers which selectively diminish the low energy portion of the bremsstrahlung spectrum.

In some aspects, a transmission detector for measuring an intensity of photons transmitted through the target sample as a function of a position on the target sample at which the photons illuminate the target sample may be provided. The transmission detector may comprise an X-ray imager.

BRIEF DESCRIPTION OF THE DRAWINGS

The invention description below refers to the accompanying drawings, of which:

FIG. 3($a$) shows the spectra of the coherent bremsstrahlung for electrons of 250 MeV incident on a diamond crystal of different thicknesses. The energy of the coherent maximum is at 60 MeV and the collimation angle is approximately $\theta_c = 0.5\theta_\gamma$;

DETAILED DESCRIPTION OF AN ILLUSTRATIVE EMBODIMENT

To provide an overall understanding, certain illustrative embodiments will now be described; however, it will be understood by one of ordinary skill in the art that the devices and methods described herein can be adapted and modified to provide devices and methods for other suitable applications and that other additions and modifications can be made without departing from the scope of the systems described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, specified, interchanged, and/or rearranged without departing from the disclosed devices or methods. Additionally, the shapes and sizes of components are also exemplary, and unless otherwise specified, can be altered without affecting the disclosed devices or methods.

Exemplary Scanning Methods and Apparatus

A beam of photons incident on a target can excite nuclear resonances or states in the target that subsequently fluoresce. The excitation spectrum and the resulting emission spectra are uniquely tied to the specific isotopes contained in the target. When detected by systems of detectors or detector arrays capable of resolving spatial information, these spectra allow for a measurement of the spatial distribution of isotopes contained in the irradiated volume.

Some exemplary systems for employing bremsstrahlung sources in resonant scattering measurements (also called nuclear resonance fluorescence or NRF) in nonintrusive scanning applications are discussed in U.S. Pat. No. 5,115,459, Explosives Detection Using Resonance Fluorescence of Bremsstrahlung Radiation, and U.S. Pat. No. 5,420,905, Detection of Explosives and Other Materials Using Resonance Fluorescence, Resonance Absorption, and Other Electromagnetic Processes with Bremsstrahlung Radiation, the contents of both of which are hereby incorporated by reference.

Figure 9:
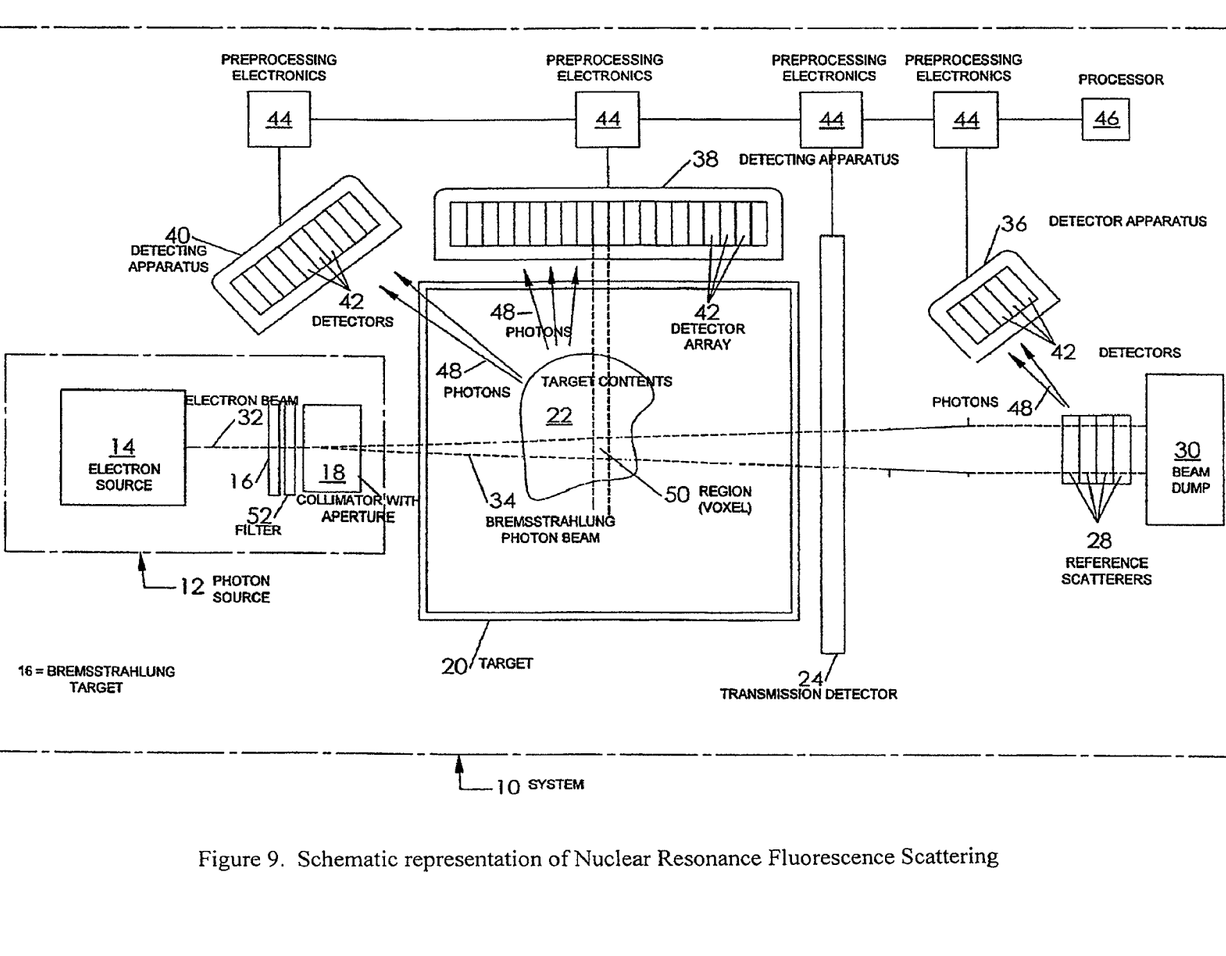
FIG. 9 is a schematic representation of Nuclear Resonance Fluorescence Scattering.

A schematic diagram of an exemplary embodiment of a nuclear resonance fluorescence imaging (NRFI) scanner configuration is shown in FIG. 9.

The system 10 includes a photon source 12 producing photons having an energy spectrum over some energy range. Suitable photon sources include: a bremsstrahlung source; a Compton-broadened photon source using nuclear decay from a radioactive source; coherent bremsstrahlung radiation; free electron lasers; laser backscatter from high energy electrons; neutron capture photons; or other photon sources known to those skilled in the field. As will be discussed further below, an NRFI scanner system may employ a narrow-band photon source or a nearly monochromatic photon source, which may also be tunable to select energies of interest for particular scanning applications.

In the embodiment illustrated in FIG. 9, the photon source 12 may be a bremsstrahlung source and may include an electron source 14 providing a beam of electrons 32 incident on a bremsstrahlung target 16 to generate a bremsstrahlung photon beam 34. The bremsstrahlung target 16 may be followed by a beam stopper (not illustrated) to stop the electrons 32. A filter 52 may follow the beam stopper to filter out low energy photons from the bremsstrahlung beam 34 or preferentially absorb photons in certain energy regions corresponding to selected NRF lines. A collimator 18 may be employed to collimate the bremsstrahlung beam 32. Shielding (not illustrated) may enclose the photon source 12. A description of an exemplary suitable bremsstrahlung photon source may be found in U.S. Pat. No. 5,115,459. Other photon sources, including narrow-band or nearly monochromatic photon sources which may also be tunable, are described below and may be substituted for the bremsstrahlung source shown in FIG. 9.

A target 20 to be scanned, such as a cargo container, shipping container, luggage, package, or other container or object, may be placed in the path of the photon beam 34. In one embodiment, the target may be moved through the path of the beam, for example by a conveyor belt. In another embodiment, the beam 34 may be scanned across the target 20, for example, by moving photon source 12 or steering the electron beam 32. The target 20 may contain target contents 22. Other ways of achieving scanning of the photon beam 34 over the target container 20 will be recognized by those skilled in the art. The incident photon beam 34 resonantly excites the nuclei of the target's contents 22, and photons 48 may be both scattered from the contents 22 and the target 20 as well as transmitted through the contents 22 and the target 20. The energies of the scattered photons are characteristic of the spacings between the quantized energy states of the nuclei of the target contents 22 and the target 20. Each isotope present in the target contents 22 resonantly scatters photons in a unique set of energies.

Detecting apparatuses 38 and 40, which may include an array of detectors 42, may capture, measure, count, and/or record the energies of the photons scattered in a given direction or directions. A description of several exemplary suitable detecting apparatuses may be found in U.S. Pat. No. 5,115,459. The detecting apparatus 38 or 40 may further include a filter over the face of each detector to absorb low energy photons, and shielding (not illustrated). As scattering from the collimating aperture 18 could lead to a significant amount of photons directed toward the detecting apparatus 38 or 40, a shadow shield (not illustrated) between the collimator and the detecting apparatus 38 or 40 may be employed. A beam dump 30 may be provided to absorb the energy of the beam 34 that is not absorbed as the beam 34 passes through the target 20. Shielding (not shown) may enclose the entire device while allowing convenient means for the entry and exit of targets. Data from the detecting apparatus 38 or 40 is sent to a processor 46 which may analyze the data. One analysis may include determining the abundances of particular nuclear species of interest. The data may be preprocessed by preprocessing electronics 44, which may include preamplifiers, filters, timing electronics, and/or other appropriate preprocessing electronics. The processor 46 may be adapted to evaluate the data to determine whether the contents of the target volume meet or exceed one or more predetermined detection thresholds. For example, the processor 46 may compare the data for each irradiated target volume to profiles of "normal" target volumes to determine whether the irradiated target volume should be considered "suspicious" or an item of interest. In addition, the processor 46 may be programmed with other threat detection heuristics as described below. Further, as described in more detail below, the processor 46 may control a variety of parameters of the photon beam, scanning, detection, and/or other aspects of the system.

In order to minimize the effects of Compton scattering and other scattering processes and maximize the signal-to-noise ratio, the detecting apparatus 38 or 40 may be placed at an angle with respect to the photon beam 34 of more than 90 degrees relative to the direction of the photon beam.

The beam 34 passes through the target contents 22. This beam may be absorbed in a beam dump 30 designed to absorb substantially all of the remaining energy. For example, a suitable beam dump for 10 MeV may include a layer of a hydrogenous material containing boron or lithium, a layer of carbon, and a layer of iron in a very deep cavity formed in a shield of lead and/or iron to shield the sides and the detectors from back-streaming low energy photons. A layer of a hydrogenous material containing boron or lithium may surround the outside of this shield. The depth of this cavity, the beam dimensions, the directive collimation of the detectors, and the exact location of the detectors are related parameters that may be made compatible so as to minimize the number of backward-streaming photons from the beam dump entering the detectors. Additional shadow shields may be set up to help meet this goal.

Imaging can be achieved in a variety of ways with the technique described herein. The luggage can be scanned with the beam by moving the entire photon source 12, the target 20, or simply the aperture 18. The electron beam may also be deflected by a magnet to sweep the photon beam direction. Preferred photon beam geometries include spots (cones) and stripes. Other suitable scanning configurations, geometrics, and patterns may be recognized by those skilled in the art and may be employed.

For example, if the beam 34 is collimated using a small circular aperture 18 to an average angle of approximately 1/20 radians (about 3 degrees), the spot 1 meter from the aperture will be about 10 cm across, a suitable size for imaging the contents of a piece of luggage or the contents 22 of a container 20.

If the photon beam 34 is collimated using a vertical slit aperture to produce a thin stripe of 10 cm width at the point of incidence with a piece of luggage, for example, a 60 cm long suitcase could be scanned in a few seconds as the suitcase moves on a conveyor belt. Alternatively, the photon beam 34 could be collimated into a spot swept vertically by an adjustable collimator or by magnetic deflection of the electron beam 32 used to generate the photon beam 34. Even if the collimation is in the form of a vertical stripe, the central intensity remains the highest, reflecting the natural collimation, and magnetic deflection of the electron beam 32 may be useful for imaging. If the collimation is a vertical stripe or a stripe of another orientation, the intersections of the stripe with the collimated views of the detectors 42 define voxels that are also useful for imaging.

In another technique, a large portion of the target container 20 may be flooded with radiation from the photon source 12 by using a large aperture, and the detectors 42 may be adapted to be direction-specific by, for example, introducing a collimator in front of each detector 42. In this way, each detector can be designed to only detect photons scattered from a small specific region 50 of the target contents 22 in a particular direction. Each such specific region or "voxel" 50 may be conceptualized as the three dimensional intersection of the photon beam 34 with the line of sight of a collimated detector 42. An array of such detectors can be designed to image the entire target 20 to a desired degree of resolution.

Use of a rapidly adjustable photon beam collimating aperture 18 results in further embodiments with important advantages. For example, a target 20 could first be flooded with radiation from the photon source 12 in an effort to detect explosives in the form of thin sheets and/or to obtain an initial estimate of the abundances of various elements in its contents. The collimating aperture 18 could then be stopped down to image the suitcase in an effort to detect more localized explosive materials. In one embodiment, the processor 46 may control the size of the collimating aperture 18 in response to any positive signal detected in an initial low-resolution scan.

The processor 46 may be adapted to analyze the data obtained by the detecting apparatus in any combination of 38 and/or 40. As with other explosives detecting devices, profiles of elements, such as nitrogen and oxygen, as they appear in "normal" target volumes or voxels may either be modeled or experimentally determined. A target volume or voxel 50 or a combination of volumes or voxels 50 which deviates significantly from these profiles may be identified as "suspicious" or an item of interest. The processor 46 can be adapted to compare data to stored profiles. If the profiles are rigorously determined, a high probability of explosives detection ("detection probability" or "DP") accompanied by a low rate of false alarms ("false positives" or "FP") may be achieved. If a region of a target shows the explicit elemental profile of an explosive the threat identification may be determined.

The detection methods thus described, in which resonant scattering from the target 20 and target contents 22 is detected by detectors 40, may be employed to obtain three-dimensional NRF imaging of the target contents 22. For example, if each detector 40 is adapted to be directional (as by collimation, for example), then the NRF spectrum detected in each detector provides a measure of the isotopes contained in each voxel 50 where the field of view of each detector 40 intersects the photon beam 34. These spectra may, if desired, be reconstructed as a 3-D isotopic image of the target contents 22. For that reason, the detection methods described above may be referred to as 3-D NRF imaging.

An alternate detecting scheme is also illustrated in FIG. 9. This alternate scheme can provide a 2-D NRF image of the isotopic composition of the target contents 22. As the photon beam 34 passes through the target 20, photons will be resonantly absorbed by the nuclei of the target contents 22. The energies of the absorbed photons correspond to the spacings between the quantized energy states of each nuclear species in the target 20. For these specific energies, the transmitted beam will be depleted of photons. For example, if the target contains nitrogen, photons of energies corresponding to the spacings between nuclear energy states in nitrogen will be selectively absorbed. The amount of photons absorbed depends on the quantity of nitrogen in the target 20. Thus, the intensities of the photons of specific energies transmitted through the target contain information about the nuclear composition of the target. A series of reference resonance scatterers 28 may be arranged behind the target 20. Each reference scatterer 28 may be composed of one or more of the elements that the explosives detecting device is to detect. An array 36 of detecting apparatuses 42 may be adapted to capture, measure, count, and record the photons 48 resonantly scattered from each of the reference scatterers 28. For example, in a simple embodiment, two reference scatterers are provided, one of nitrogen, the other of oxygen. In such an embodiment, a detecting apparatus may be adapted to detect photons resonantly scattered from the nuclei in the nitrogen scatterer and another detecting apparatus may be adapted to detect photons resonantly scattered from the nuclei in the oxygen scatterer. Alternatively, a single detecting apparatus 42 may be adapted to detect photons resonantly scattered from nuclei in all the reference scatterers 28.

This detecting scheme operates as follows. If no target 20 is placed in the path of the photon beam 34, the photon beam will directly strike the first of the reference resonance scatterers 28. The detecting apparatus 36 associated with the first reference scatterer will detect a relatively large amount of photons corresponding to a nuclear species contained in the first reference scatterer, because there will have been essentially no absorption at energies corresponding to such a species. Likewise, if a target 20 containing only a relatively small amount of a nuclear species contained in the first reference scatterer is placed in the path of the beam, this strong signal at the first detecting apparatus will be diminished by only a relatively small amount. If however, a target 20 with a relatively large amount of the nuclear species contained in the first reference scatterer is placed in the path of the beam, this signal will be diminished considerably, due to the resonant absorption in the target 20 of the photons of energies corresponding to that nuclear species.

Thus, an abundance of a nuclear species of interest in a target 20 and its contents 22 will be detected as a decrease in the signal from the detecting apparatus associated with a reference scatterer containing that nuclear species. Photons of energies not corresponding to the nuclear species of which a reference scatterer is substantially composed will be attenuated due to non-resonant processes by only a relatively small amount. Thus, the method of detecting the nuclear species of the first reference scatterer extends to each subsequent reference scatterer. An advantage of this detecting scheme is that if the energies corresponding to two or more nuclear species of interest are very close, the detecting apparatus 38 or 40, detecting directly scattered photons, may have difficulty distinguishing the contributions from the two or more nuclear species. However, using the transmitted photons and reference scatterer 28, the energies corresponding to each nuclear species are detected separately, this ambiguity is diminished considerably, and the ability of the detecting apparatus to resolve closely spaced photon energies is no longer very important. When the energies corresponding to two or more nuclear species do not interfere, a single reference scatterer can be composed of a combination of the species.

It is a further advantage of this detection scheme that it may allow the total amount of material of a nuclear species corresponding to a nuclear species contained in a reference target to be measured quickly and with a relatively small number of detectors. This may allow, for example, a rapid first-pass scan of the target 20 for the presence of any amount of one or more nuclear species of interest, before a more detailed scan or imaging procedure is undertaken. Where such a rapid first-pass scan shows that no threatening quantities of nuclear species of interest are present, more detailed scans may be bypassed, for a savings of time and resources.

In the embodiment illustrated in FIG. 9, the system may also include a direct transmission detector 24, such as an X-ray imager, which can measure the intensity and/or energy of photons transmitted through the target 20 as a function of the position at which the photon beam 34 strikes the target 20 (or, for a bremsstrahlung source, as a function of the position at which the electron beam strikes the bremsstrahlung target).

Such a measurement could be used by anyone schooled in the art, for example, to obtain a map of the average density of the target 20, projected along the axis of the photon beam 34. In this way, a very precise image of the transmission density of the target can be constructed. Such an image will identify specific areas of high material density in the target which would be a further aid in detecting explosive or high atomic number materials. (Similar density imaging could also be achieved by detecting the back-scatter from the target 20.)

Use of Nearly Monochromatic and Tunable Photon Sources

If NRFI scanning of cargo is performed using a source whose spectrum is narrower than the full bremsstrahlung spectrum, but is broad enough to include photons resonant with more than one species of interest, then some of the advantages described earlier of using a narrow-band source may be realized, while allowing efficient scanning for multiple species simultaneously. Where such a source is tunable, further advantages can be realized. Alternatively, NRFI scanning may be performed using a nearly monochromatic but tunable source that may be resonant with only one or a few spectral lines at a time. With such a source, detailed scans of one or a few particular species of interest may be performed without interference from the processes described above that may occur when using a photon beam with a broad spectrum such as a bremsstrahlung beam. Where such a source is tunable, species of interest and/or particular spectral lines of interest may be selected as the scan is being performed, providing both the advantage of a narrow-band source and the flexibility to scan for many species of interest in a single pass through the system.

In one embodiment, a broad spectrum source such as a bremsstrahlung source may be combined with a narrower-band, monochromatic, or nearly monochromatic source, which may be tunable. If a first-pass scan with the broad spectrum source suggests the presence of particular species of interest in threshold quantities, more particularized scans may then be conducted with the narrower-band, monochromatic, or nearly monochromatic source. Such combined use of different types of sources may increase the detection probability while decreasing the rate of false positives.

Sources of Photons with Narrow-Band, Monochromatic, or Nearly Monochromatic Energy Spectra There are a variety of methods that can be used to generate photons for use in Nuclear Resonance Fluorescence where the spectral range of the photon energies is limited in comparison to that of a standard bremsstrahlung energy distribution. These include:

1. Backscattering of laser light by energetic electrons,
2. Backscattering of free electron laser radiation from energetic electrons,
3. Coherent bremsstrahlung from periodic lattices,
4. Monochromatic or nearly monochromatic photons from particle-induced reactions in nuclei,
5. Monochromatic or nearly monochromatic photons from reactions such as (p, $\alpha\gamma$), (n,n'$\gamma$), (p,p'$\gamma$), or ($\alpha,\alpha'\gamma$),
6. Tuning the frequency and broadening the energy spectrum of a monochromatic or nearly monochromatic photon line by the angular dependence of the energy resulting from Compton scattering from electrons, and
7. Narrowing the range of the energy spectrum from bremsstrahlung by a selective use of absorbers to diminish the relative strength of the low energy portion of the spectrum relative to that at higher energies.

1) Backscattering of Laser Light by Energetic Electrons

This process relies on the Compton scattering of photons by electrons. In the laboratory system for an electron at rest, Compton scattering generally reduces the photon energy because of the recoil of the electron absorbing some energy.

When the electron is energetic, the photon can gain considerable energy from the electron. If a laser photon of energy $k_1$ is incident on a relativistic electron of energy E with a relative angle $\theta_1$ and scatters making an angle $\theta$ relative to the electron beam direction and an angle $\theta_2$ relative to the incoming photon beam direction, the energy of the final photon is:

$$k=k_1(1-\beta \cos \theta_1)/[1-\beta \cos \theta+(k_1/E)(1-\cos \theta_2)]. \quad 1$$

Figure 1:
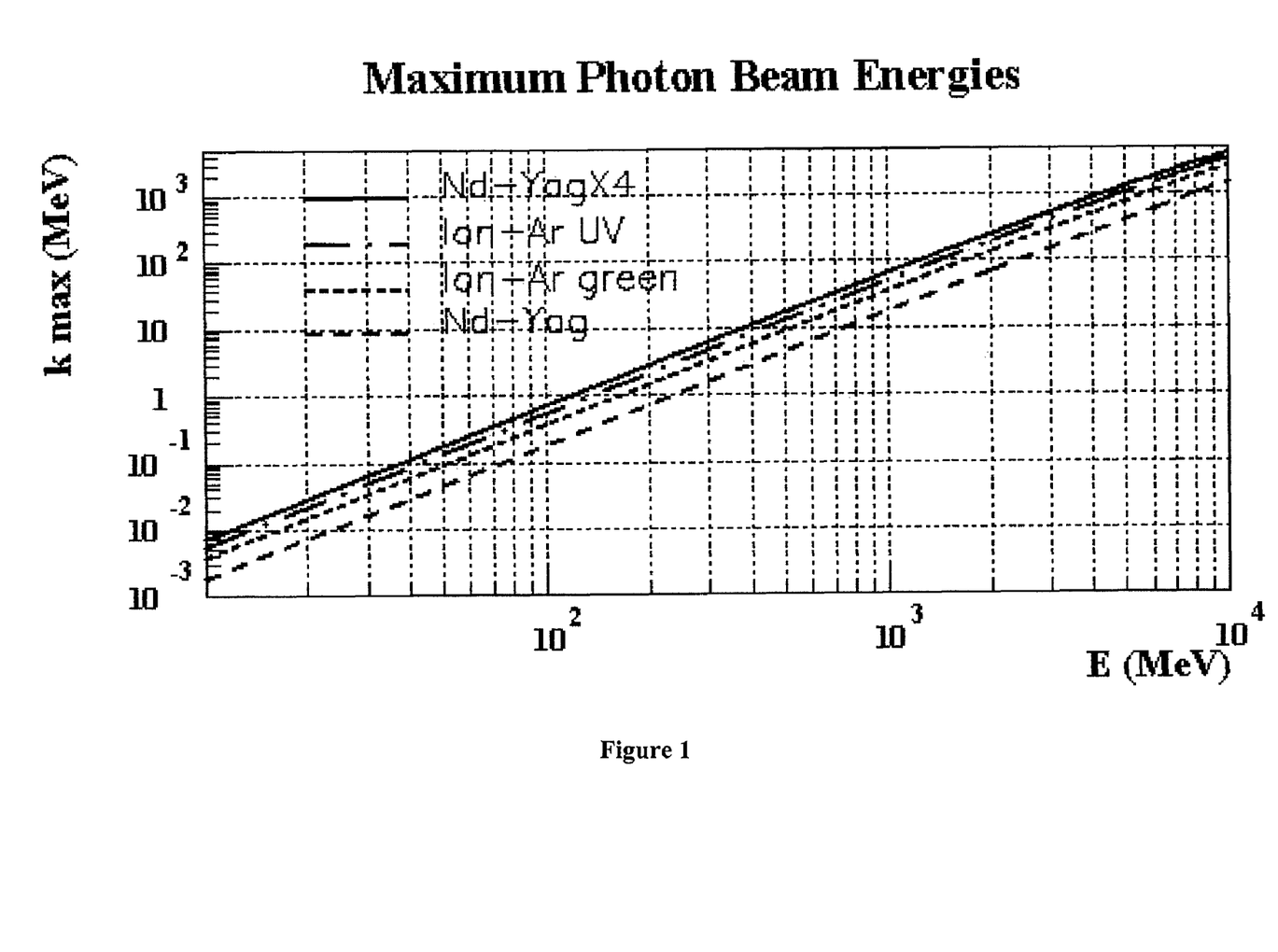
FIG. 1 illustrates maximum photon energies as a function of electron energy for various laser lines.

Here, $\beta$ is the electron velocity in units of the speed of light c and is very close to unity since $E/m_e=\gamma \gg 1$. For the conditions considered herein $\theta_1 \cong \theta_2 \cong 180°$ and $\theta \ll 1$ radian, the photon is scattered in the backward direction inside a narrow cone with the axis coinciding with the incoming electron beam. Neglecting the weak dependence on $\theta_1$, the scattered photon energy is given by:

$$k=Ez/(1+z+x), \quad 2$$

where $z=4$ $Ek_1/m_e^2$ ($m_e$=electron rest mass) and $x=(\theta_y)^2 \ll 1$. The maximum photon energy, $k_m$, is obtained when $\theta=0$. In FIG. 1 the dependence of the maximum energy of the scattered photon on electron beam energy and laser photon energy is exhibited for several examples. Review of Compton Scattering Projects; A. D'Alngelo, INFN Roma II, Via della Ricerca Scientifica, 1 I-00133 Rome, Italy.

Note that the energy range appropriate for Nuclear Resonance Fluorescence (NRF) scanning of materials can be achieved with an accelerator producing electrons of about 400 MeV. This would allow photons of more than 10 MeV to be produced using, for example, a Nd-YagX4 laser. Lower photon energies could be produced using lower electron energies and/or lower frequency lasers. The photon energy is tunable to whatever energy is desired over a broad range that encompasses most strong NRF states in nuclei.

The energy of the scattered photon beam is also determined by the angle $\theta$ as exhibited by equation 2. Energies lower than $k_m$ are available in a conical annulus centered about the electron beam direction with $\theta>0$. For example, for a photon of energy $k/k_m=0.5$, $\theta$ is approximately 1 mr using 400 MeV electrons and a laser energy of about 5.3 eV. In this case, $k_m$ is approximately 8.42 MeV and the energy of photons at 1 mr is 4.21 MeV. While this angular region appears very narrow accelerators of 400 MeV have typical emittances of 31.4/$\gamma$=0.04 mm-mr and a one mm beam presents an angular spread of only 0.04 mr, substantially less than 1 mr. Thus, collimation into annular cones is a feasibility not destroyed by the angular spread of the electron beam.

To display the energy spectrum if the photons it is useful to define the quantities:

$$a=1/(1+z)$$

$$\rho=k/k_m=1/(1+ax):$$

$$\chi=\rho^2(1+a)^2/[1-\rho(1-a)]$$

$$\cos \alpha=(1-\rho(1+a))/(1-\rho(1-a)).$$

Then the total energy spectrum is expressed in these terms by the cross section in the laboratory frame for Compton scattering:

$$d\sigma/dk=[(2\pi)(r_e)^2 a/k_m](1+\chi+\cos^2\alpha); \text{ where } r_e=2.818 \text{ fm}.$$

This spectrum is slowly varying compared to a bremsstrahlung beam and avoids the large low-energy increase that contributes to backgrounds and unnecessary radiation exposure. Furthermore, the spectrum can be limited in range and tuned in energy by appropriate collimation.

2) Backscattering of Free Electron Laser Radiation from Energetic Electrons.

If a free electron laser is used, the laser photon energy is given by the relation:

$$k_1=chk_\omega\gamma^2/(\pi(1+(a_\omega)^2),$$

where $k_\omega$ is the undulator wave number, and $a_\omega$ is the normalized rms vector potential of the undulator. Basically all the concepts discussed in the previous section obtain with the added advantage of greater intensity being possible than with conventional lasers. This technique for obtaining a tunable photon beam has been demonstrated in nuclear physics research labs. Parity Measurements of Nuclear Levels Using a Free-Electron-Laser Generated $\gamma$-Ray Beam: A. W. Wright et. al., Phys. Rev. Lett., 88, 1 Jan. 7, 2002 (012502-1)

3) Coherent Bremsstrahlung from Periodic Lattices.

When an electron passes through a properly oriented crystal lattice, the radiation from each lattice site produces a coherent wave that enhances the photon yield at certain photon energies and at unique directions. Coherent Bremsstrahlung at Low Energies: A. W. Saenz and H. Uberall, Phys. Rev. B 25, and A Coherent Bremsstrahlung Beam at the MAX-LAB Facility, V. V. Denjak, V. B. Ganenko, S. V. Kas'jan, V. I. Morochovskij, I. N. Shapoval, NSC "Kharkov Institute of Physics and Technology", Kharkov 61108, Ukrain. Generally the emission of coherent bremsstrahlung peaks at an angle of approximately $mc^2/E_0$, where $E_0$ is the electron energy. The coherent radiation is distributed in a very narrow angular region with optimal angle of approximately $\theta c \sim 0.5\theta_y$. These features are illustrated in FIG. 2, which is taken from FIG. 8 of Saenz and Uberall, by a theoretical calculation for an electron beam energy of 15 MeV.

Figure 2:
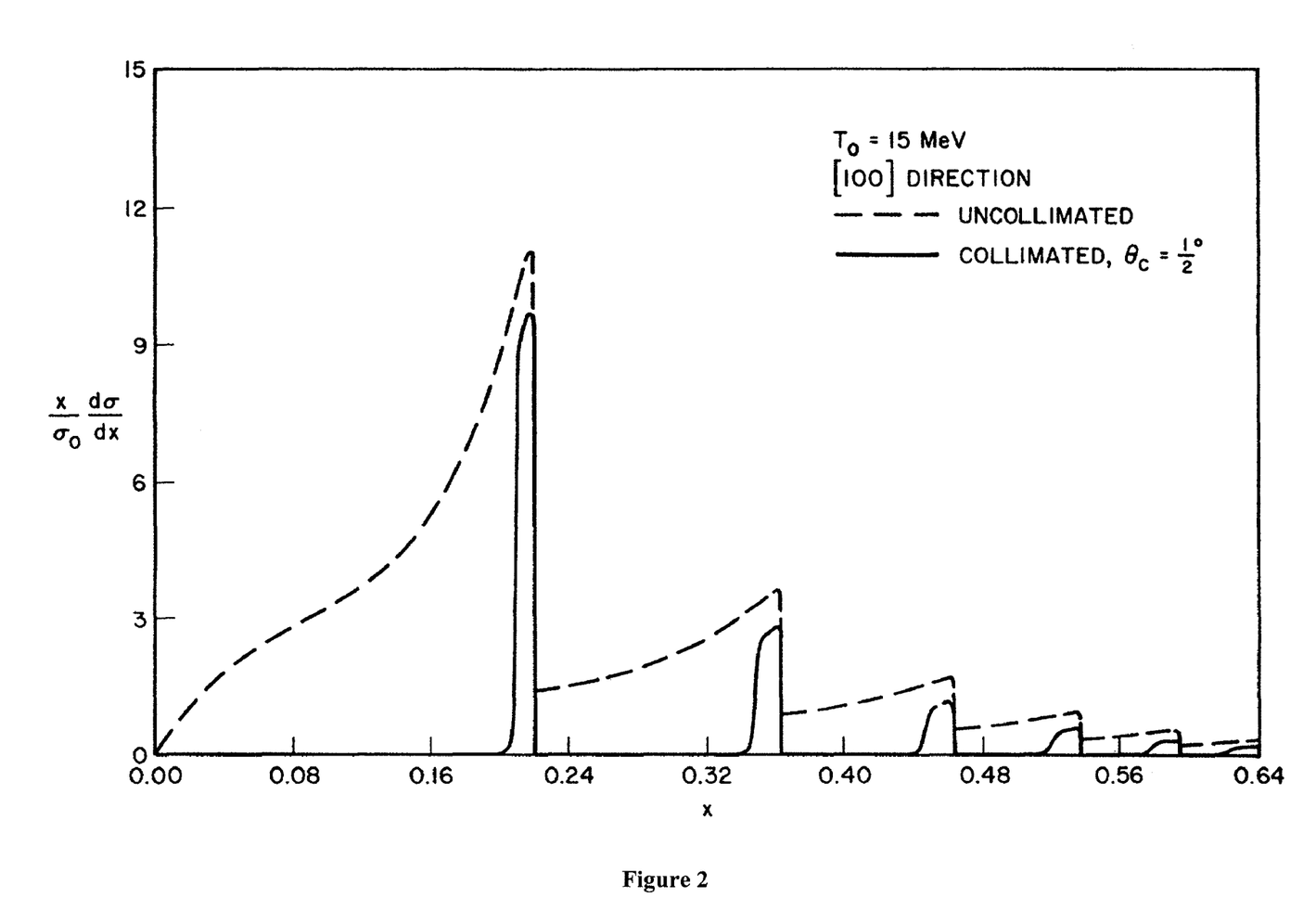
FIG. 2 is a diagram of emitted bremsstrahlung collimated by $\theta_c \sim 0.5°$ for a Si crystal.

In FIG. 2; $x=E_y/E_0$, $\sigma_0=Z^2(1/137)(e^2/mc^2)^2$, $\tau_0=E_0$, and $d\sigma/dx$ is the total cross section leading to photons in the collimated (uncollimated for dashed curve) region. The collimated spectrum has unique regions where there are photons and very little intensity between these regions. By selecting the crystal lattice and its orientation, and/or by tuning the electron energy, these regions of almost monochromatic photons can be tuned to any energy desired.

Figure 3A:
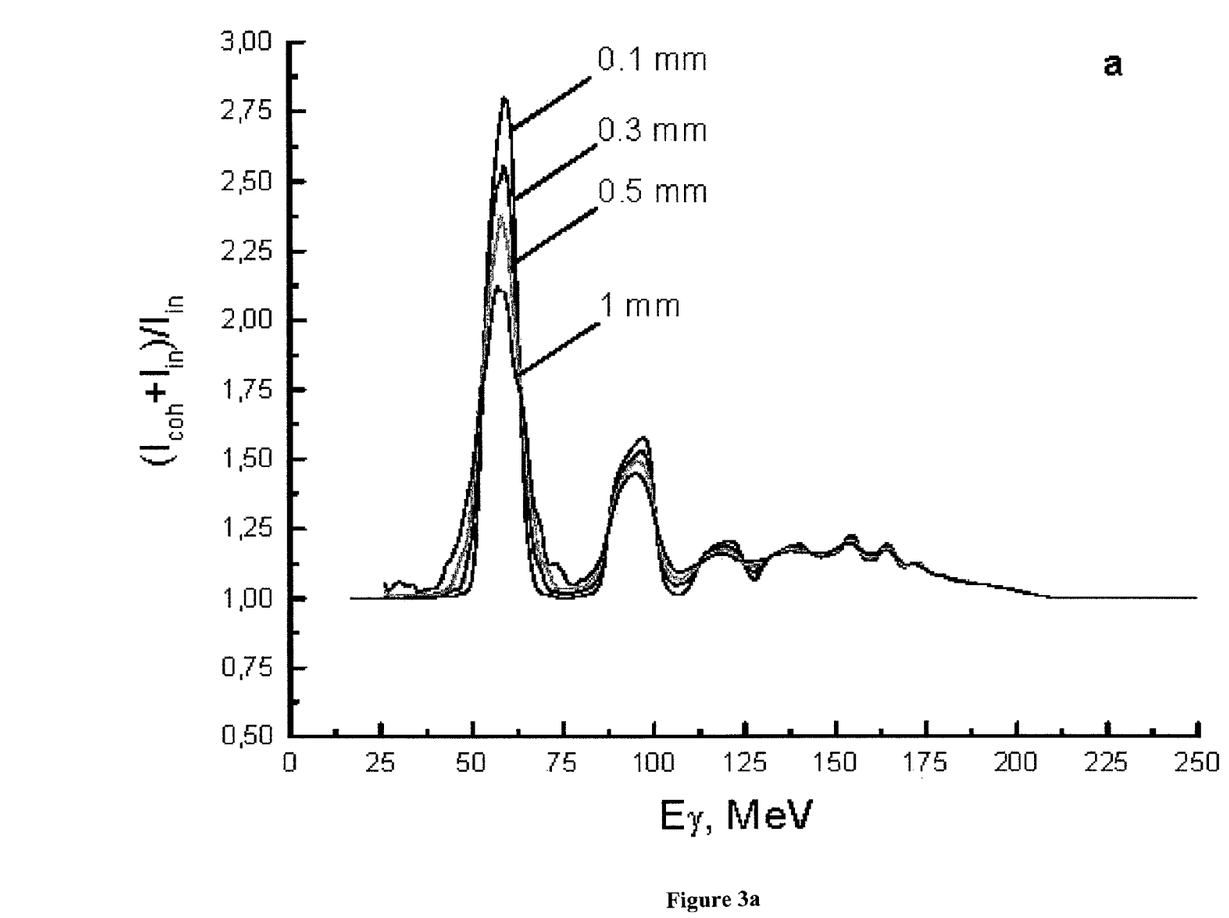
Figure 3B:
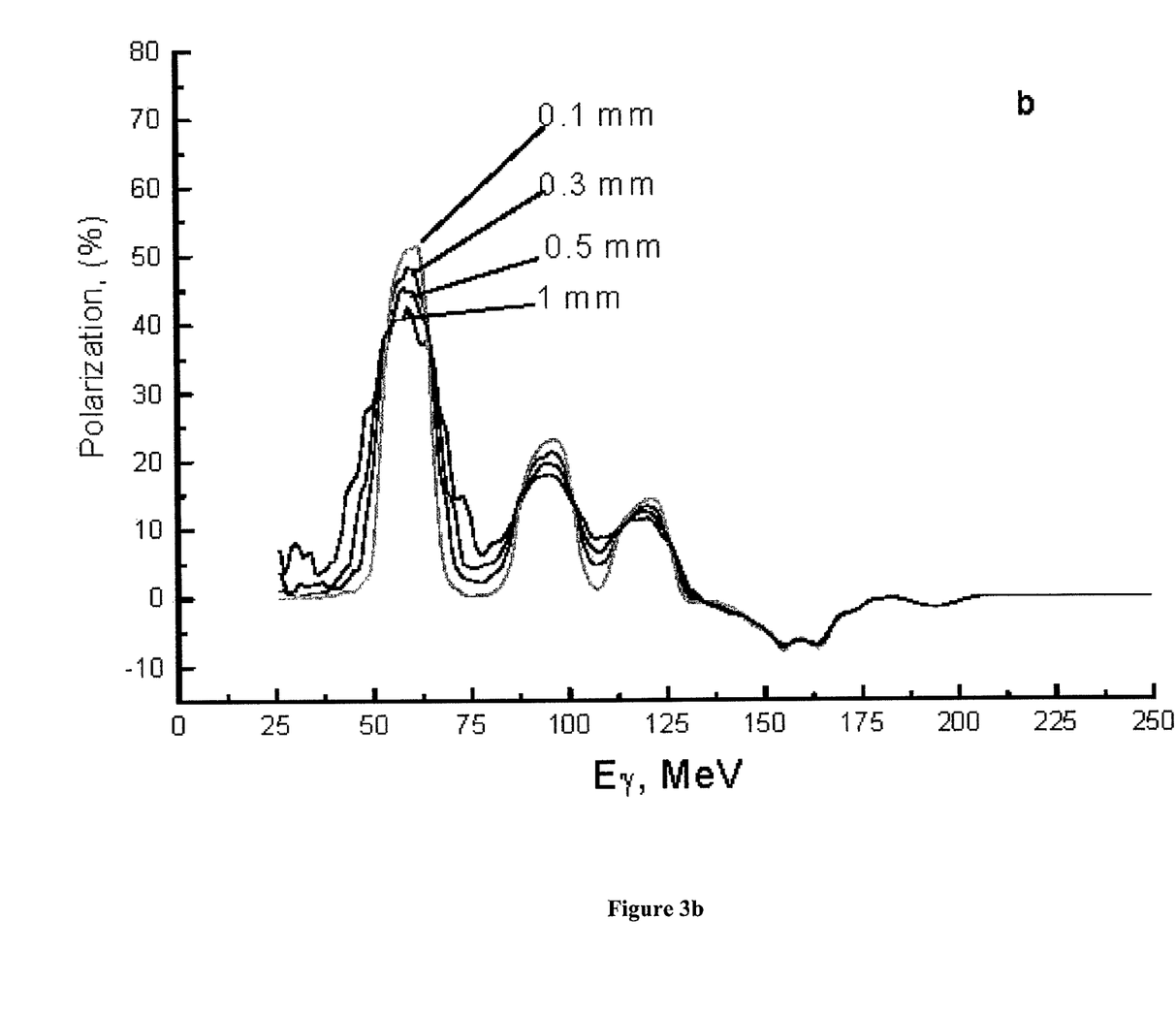
FIG. 3(b) shows the polarization of the coherent bremsstrahlung for electrons of 250 MeV incident on a diamond crystal of different thicknesses. The energy of the coherent maximum is at 60 MeV and the collimation angle is approximately $\theta_c = 0.5\theta_\gamma$.

In FIGS. 3a and 3b, the expected spectrum of photons, and the polarization of the coherent bremsstrahlung, is demonstrated for electron beams of 230 MeV incident on diamond crystals of various thicknesses.

The abscissa of FIG. 3a is the ratio of the sum of the coherent and incoherent radiation to the incoherent radiation. This is called $\beta$ in Table 1 below that exhibits the intensities and polarizations observed at various photon energies. These FIGS. 3a and 3b and Table 1 with annotations are taken from J.-O. Adler et al., Report 01/01 LUNFD6/(NFFR-3086)/1-31/2001, which reports details of the experimental measurements therein. They are reproduced in A Coherent Bremsstrahlung Beam at the MAX-LAB Facility, V. V. Denjak, V. B. Ganenko, S. V. Kas'jan, V. L. Morochovskij, Yu. P. Peresyn'ko, I. N. Shapoval, NSC "Kharkov Institute of Physics and Technology", Kharkov 61108, Ukraine.

TABLE 1

Expected intensity and polarization of the CB beam (see text).

| $E_\gamma$, MeV | 20 | 40 | 60 | 80 | 100 |
|---|---|---|---|---|---|
| $I_{in}$, $10^6$ $\gamma$/MeV/s | 3.42 | 1.58 | 1.00 | 0.69 | 0.52 |
| $\beta_{max}$ | 4.25 | 3.5 | 2.66 | 2.16 | 2.04 |
| $I_{cob} + I_{in}$, $10^6$ $\gamma$/MeV/s | 14.5 | 5.53 | 2.66 | 1.49 | 1.06 |
| $P_\gamma$, % | 75 | 69 | 58 | 48 | 38 |

The result of these calculations and experimental efforts have demonstrated fluxes of nearly monochromatic photons in the range of $10^6$-$10^7$ photons/MeV with beam currents of no more than 40 na. The photon beams generated by this process are highly collimated and tunable.

4) Monochromatic Photons from Particle-Induced Reactions in Nuclei.

When a thermal or low-energy neutron is captured in a nucleus, photon emission is a very probable possibility. Generally there are many states available for photon decay and many photon lines are produced. These photons can be resonant with excited states in other nuclei of interest or they can be sufficiently close to resonances so as to have significant cross sections for nuclear resonance fluorescence. With a prolific source of neutrons, the photons emitted from neutron capture can be a powerful source for the use of nuclear resonance fluorescence in the detection of elemental contents of contained materials.

Figure 4:
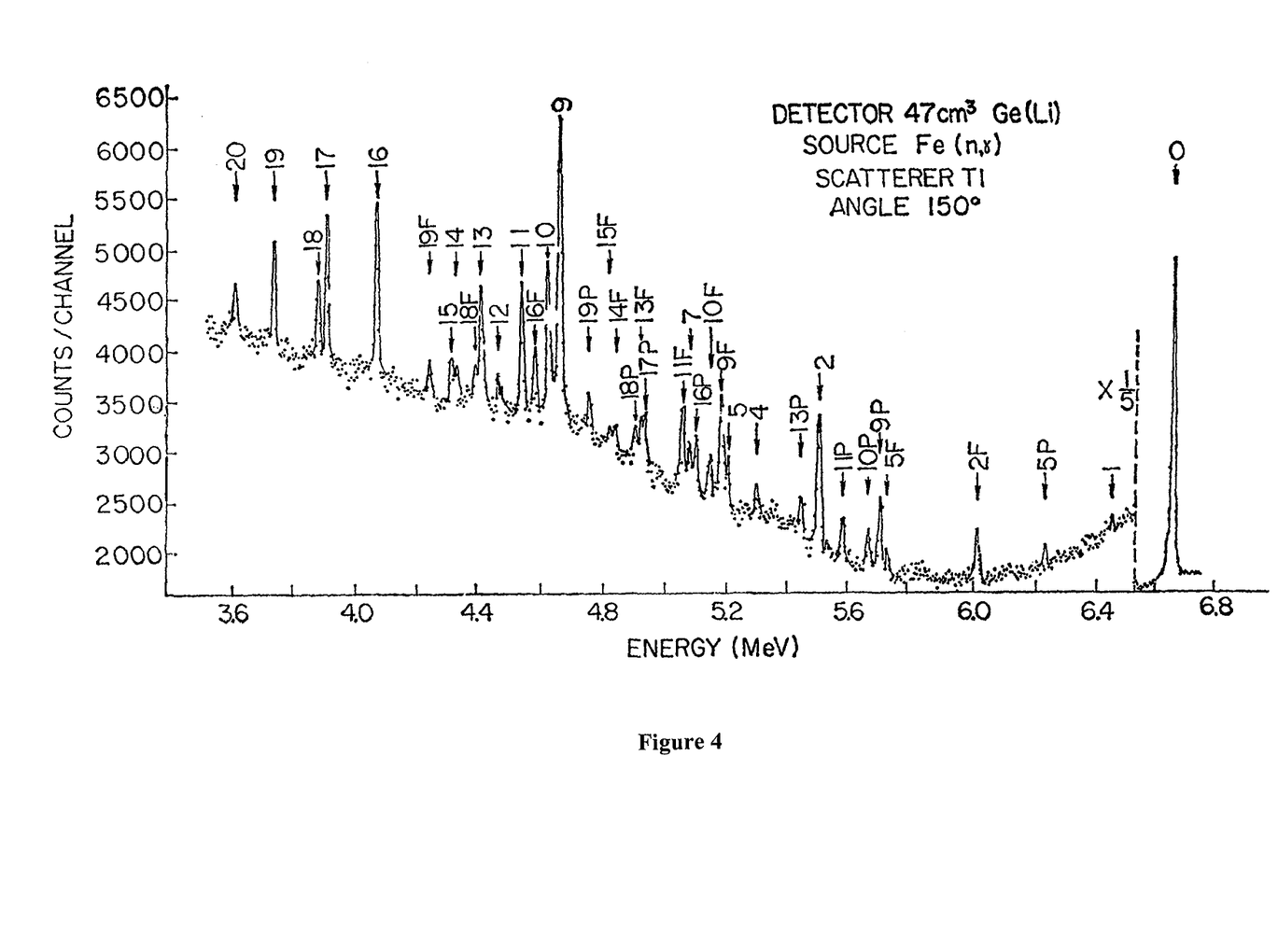
FIG. 4 illustrates studies of nuclear resonance fluorescence in T1 using lines from Fe(n,γ)

The process of neutron capture has been successfully used to provide monochromatic or nearly monochromatic photon beams for studies of nuclei with NRF. R. Moreh, S. Shlomo, and A. Wolf, Phys. Rev. C 2, 3 1970 (1144) and references therein, B. Arad, G. Ben-David, Rev. Mod. Phys. 45, 2, 1973 (230) and references therein. For example, with a reactor having a thermal neutron flux of $10^{13}$/sec/cm$^2$, 10 kg of iron produces 7.632 MeV photons with a flux of approximately $10^8$/sec/cm$^2$ at 5 meters from the iron target. The shape of the lines is given by thermal and zero-point energy Doppler broadening with a width of 4-8 eV in the case of an iron target. An example of studies of nuclear states in T1 using the lines created by Fe(n.$\gamma$) is given in FIG. 4. R. Moreh and A. Wolf, Phys. Rev. 182, 4, 19659 (1236) In the illustrated example the scattering angle from T1 is 150 degrees and the detector was 47 cm$^3$ of Ge(Li).

With the variety of nuclei that have strong thermal neutron capture cross sections and many photon lines it is possible to find photon energies that are within the reach of many excitations in nuclei that are Doppler broadened from 4 to 20 eV depending on molecular structure and nuclear mass.

An advantage of a (n,$\gamma$) source over a broadband source is that it has photons concentrated within a few eV of the energies that are needed and potentially can avoid causing as much radiation exposure as a broadband source such as bremsstrahlung radiation.

If the (n,$\gamma$) reaction photons are not close enough to specific NRF states in the energy width provided by Doppler broadening they can be shifted in energy by tuning using Compton scattering as described in (6) below.

Commercial sources of neutrons are available from the (d,t) reaction and the (d,d) reaction that have respectively $10^{10}$ and $10^8$ neutrons/second. A reasonable thermal flux from such sources properly moderated is shown by Monte Carlo calculations (MCNP, Monte Carlo N-Particle Transport Code System, Oak Ridge National Laboratory) to provide for many geometries a very usable source of photons via the (n,$\gamma$) reaction as described above.

Figure 5:
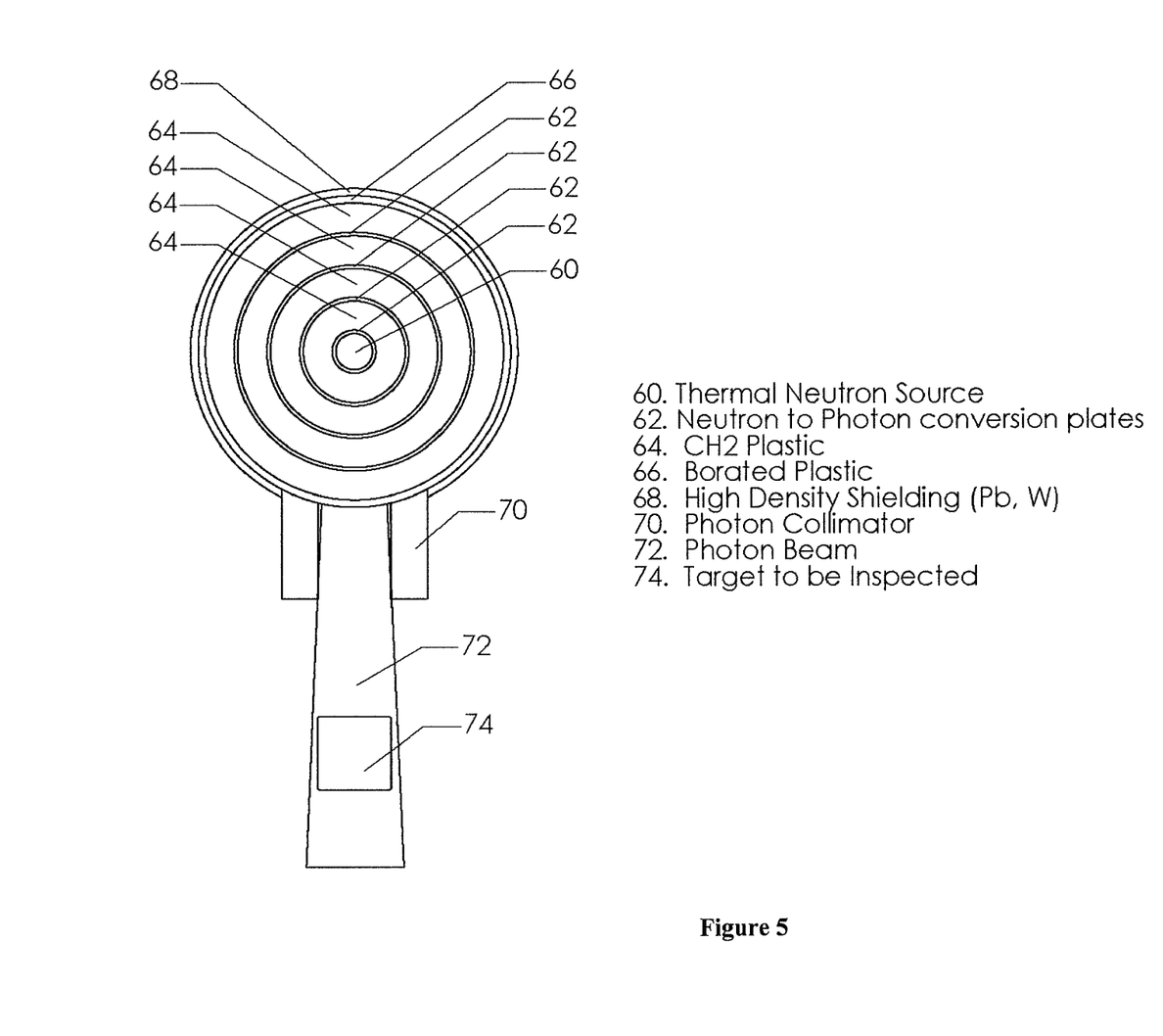
FIG. 5 is a schematic design of an exemplary system to provide (n,γ) photons.

The schematic design of an exemplary system to provide (n,$\gamma$) photons is illustrated in FIG. 5. The system includes a neutron generator 60 as described above which may be surrounded by layers of hydrogenous material 64, such as a plastic, with basic composition CH$_2$. The hydrogen serves to thermalize the neutrons and the carbon acts as a reflector. Multiple layers of another material 62, in which the (n,$\gamma$) reaction takes place, may be spaced at intervals. In an exemplary embodiment the layers of the reaction material may be spaced regularly at, for example, 10 cm intervals. In the examples cited above the reaction material was iron. However, other materials will provide other photons at other energies of interest. In an exemplary embodiment the entire reactor sphere is one meter in diameter. It may be surrounded by shielding material 66, such as borated polyethylene, to shield against escaping neutrons. There also may be a shield 68 of lead or other high density material, at the outermost radius, as in the embodiment illustrated in FIG. 5, to prevent the escape of photons, and a collimator 70. One region may be left unshielded so that the photon beam 72 may escape to the target 74 to be irradiated for the NRF reaction.

While this discussion has described neutron capture, other reactions induced by particle capture in the nucleus also may be used to generate photons.

5) Monochromatic Photons from Reactions Such as (p, $\alpha\gamma$), (n,n'$\gamma$), (p,p'$\gamma$), or ($\alpha$,$\alpha'\gamma$).

Generally, when a reaction excites a state of a nucleus and that state emits a photon, this photon energy is no longer resonant with another nucleus of the same species. This is due to the recoil of the emitting nucleus Doppler shifting the photon. The recoil momentum has a contribution from the photon emission process and from the momentum imparted by the bombarding particle such as in the (p, $\gamma$) process. In the latter reaction, the two body final state allows the recoiling photon to be shifted back onto resonance at very specific angles and for narrow ranges of angles. However, processes with three body final states such as (p, $\alpha\gamma$), (n,n'$\gamma$), (p,p'$\gamma$), or ($\alpha$,$\alpha'\gamma$) may produce a Doppler shift of the photon energies at any angle since all possible recoil momenta are available for any angle of photon emission. A specific example is the $^{19}$F(p, $\alpha\gamma$) process used to study the properties of the 6.9 and 7.1 MeV states of $^{16}$O via NRF. C. P Swann and F. R. Metzger, Phys. Rev., 108, 4, 1957 (982) FIG. 6, taken from FIG. 1 of Swann and Metzger, shows approximately the spectra of photons produced because of the three-body final state in this reaction.

Figure 6:
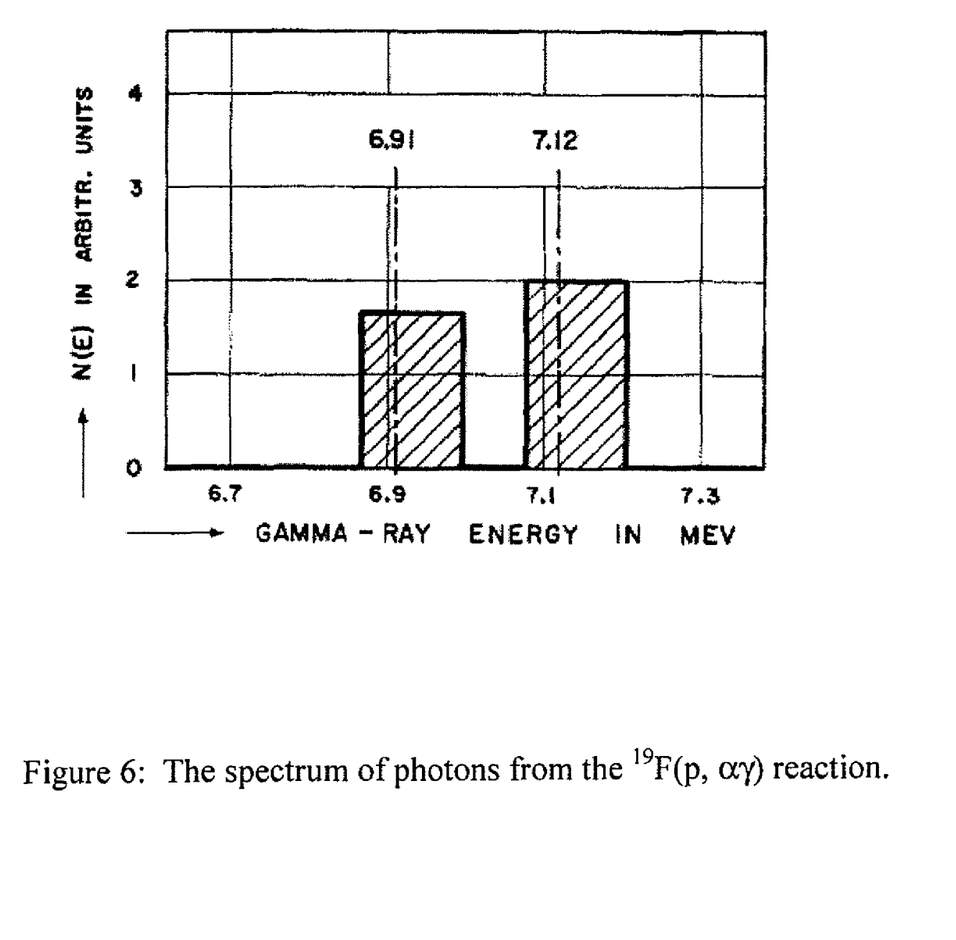
FIG. 6 illustrates the spectrum of photons from the $^{19}$F(p, αγ) reaction.

These results are typical of the reaction types considered herein with three-body final states. The resonant photons are specific to the nuclear species of interest but they are broadened by the kinematic conditions over ranges of approximately 100 keV that overlaps at all angles the very narrow NRF states of the nucleus. A reduction in unwanted photons by as much as a factor of 50 is possible compared to bremsstrahlung but the intensity covering the narrow NRF lines is generally considerably less. This reaction has a very approximate yield of 7 MeV photons using protons of 2.9 MeV of $10^{-7}$ photons per proton. C. Y. Chao et al., Phys. Rev. 79, 1, 1950 (108)

6) Tuning the Frequency and Broadening the Energy Spectrum of a Monochromatic Photon Line by the Angular Dependence of the Energy Resulting from Compton Scattering from Electrons.

Compton scattering of photons from the electrons in a material will shift the photon energy because of the recoil energy imparted to the electrons. The relationship between the energy of the scattered photon, E, and the energy of the incident photon, $E_0$, and the scattering angle, $\theta$, is given by:

$$E = E_0/[1-(E_0/mc^2)(1-\cos\theta)].$$

Figure 7:
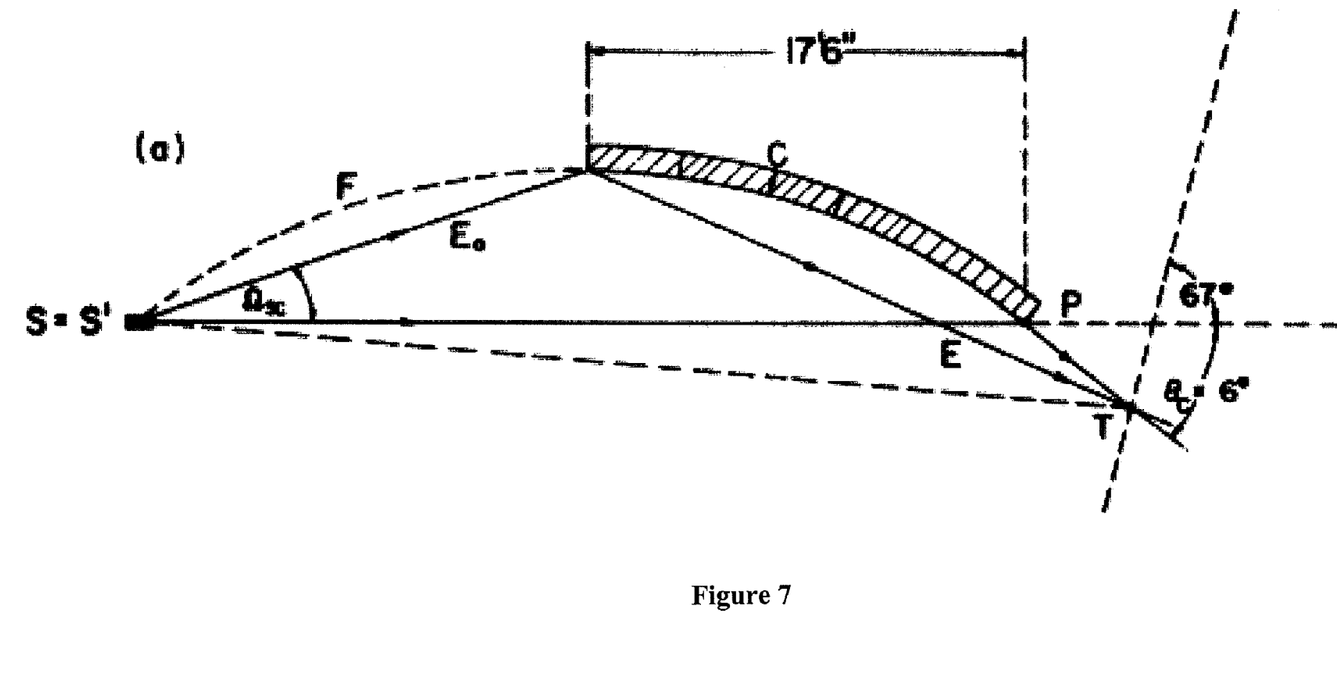
FIG. 7 illustrates Compton scattering geometry used to "focus" the scattering at a specific angle.

Thus, any monochromatic (or nearly monochromatic) line or combination of lines can be "tuned" to any energy from $E_0$ to approximately 0.25 MeV depending on the scattering angle (assuming that $E_0$ is well above $mc^2$). One can also use the relationship to enhance the scattered intensity by using a variant of the geometric arrangement employed by Knowles and Ahmed. J. W. Knowles and N. M. Ahmed, 1966, Atomic Energy of Canada Ltd., Report 2535. This is shown in FIG. 7, taken from Knowles and Ahmed.

The photon source is at S and the target at T; the geometry of the scattering arc C is arranged so that all photons arriving at T by scattering have the same Compton scattering angle and thus are degraded in energy by the same amount. The resolution of a photon line is changed by the acceptance width of the scattering angle of the experimental arrangement. The photons from the source have energy $E_0$ and the scattered photons energy E. The resolution of a photon line is changed by the acceptance width of the scattering angle of the experimental arrangement. F is the focusing circle and the scatterer C is curved to match this circle. In this particular example the dimension of the scattering arc is 17' 6" and the Compton scattering angle, $\theta_c$, is 6 degrees; the source and pivot P are fixed; and, the target can move along the fixed line at 67 degrees with respect to the line joining S and P. The angle $\Omega_{SC}$ is the angle subtended by the curved scatterer C.

7) Narrowing the Range of the Energy Spectrum from Bremsstrahlung by a Selective Use of Absorbers to Diminish the Relative Strength of the Low Energy Portion of the Spectrum Relative to that at Higher Energies.

The NRF technique may use photons with many different energies. In many applications these energies are above approximately 1 MeV. The bremsstrahlung spectrum, however, is comparatively more intense at lower energies. Therefore it may be advantageous to remove the low energy photons from the spectrum relative to the useful higher energies by a filter in the photon beam. This reduction can reduce the unwanted counting rate from scattering into detectors, thus reducing dead times. It may also reduce the unwanted radiation dose to any object being examined by NRF. Preferably, a filter for removing low-energy photons from a bremsstrahlung source uses to advantage the strong increase with decreasing photon energy of the photoelectric effect, and thus a heavy element is a desirable component of such a filter. A filter also may make use of a lighter element to take advantage of the strong dependence of pair production on nuclear charge, Z. The combination of one or more comparatively heavy elements and one or more comparatively light elements in "graded filters" removes low energy components of the bremsstrahlung beam by the photoelectric effect in a high-Z material and removes the 0.5 MeV component strongly produced in the high-Z material by pair production and the radiative effects of these pairs. Such a graded filter may also be useful in the path of photons scattered from a target into the photon detectors. Here it serves a similar function and removes preferentially the low energy portion of the scattered photon spectrum caused by Compton scattering, multiple processes and pair production in the scattering target.

Figure 8:
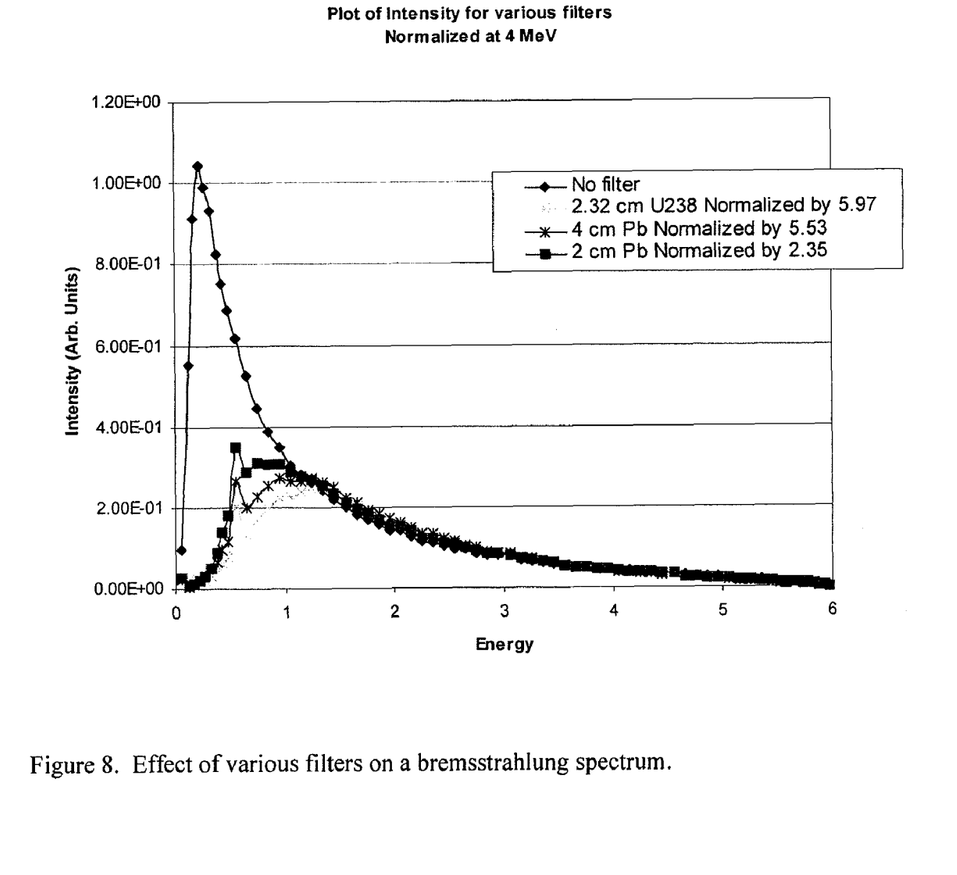
FIG. 8 illustrates the effect of various filters on a bremsstrahlung spectrum.

FIG. 8 illustrates the process for two different absorbers at high values of atomic number Z (82 and 92). The illustrated spectra are the result of MCNP calculations. FIG. 8 compares the filtered flux to the original flux from a bremsstrahlung target composed of a few mils of gold backed by a 1-cm thickness of copper to stop the electron beam. The photon flux below one MeV is greatly reduced in these examples compared to the spectrum with no filters. The use of such filtered bremsstrahlung spectra in NRFI scanning may have several advantages, including: a large reduction of the photons providing unwanted or excess radiation dose to a sample; and a large reduction of the counting rates of unwanted photons at low energy in a detector viewing the scattering sample. The peaks at about 0.5 MeV are due to positron production and annihilation in the absorbers. These peaks can also be reduced by including a layer of lower-Z materials following the high-Z materials in the filter. A desired intensity in the region of 4 MeV can be maintained by increasing the current in the electron beam used to generate the bremsstrahlung beam, to compensate for the attenuation of the filters in this energy range. The normalization factors reflect approximately the amount the beam must be increased for each filter to obtain the same photon yield at 4 MeV as the original unfiltered bremsstrahlung spectrum.

The invention claimed is:

1. A method for detecting a potential item of interest in a target sample, the method comprising:
    a) providing a first source of photons, configured to generate photons by at least one of: Compton scattering of photons by electrons; passage of a beam of electrons through a periodic lattice; and a particle-induced reaction in a nucleus,
    wherein the first source photon frequency is tunable to a plurality of specific energies of interest;
    b) providing at least one photon detector to measure an intensity of photons scattered from at least a portion of the target sample in at least one energy channel;
    c) tuning the first photon source to a first specific energy of interest corresponding to a nuclear resonance in a first nuclear species of interest;
    d) illuminating the target sample with photons from the first photon source having the first specific energy of interest;
    e) upon the intensity of photons detected in at least one of the at least one detector energy channels of interest meeting a predetermined first nuclear species of interest detection criterion, determining that the first nuclear species of interest has been detected;
    f). upon the intensity of photons detected in all energy channels of interest not meeting the predetermined first nuclear species of interest detection criterion, repeating steps d) to e) with the first photon source tuned to a further specific energy of interest corresponding to a nuclear resonance in a further nuclear species of interest.

2. The method of claim 1, wherein the first source photons are generated by backscattering of laser photons by energetic electrons.

3. The method of claim 2, wherein the first source photon frequency is tuned by varying the electron energy.

4. The method of claim 2, wherein the first source photon frequency is tuned by varying the laser photon energy.

5. The method of claim 2, wherein the first source photon frequency is tuned by varying an angle of backscattering.

6. The method of claim 5, wherein the angle of backscattering is varied by collimation.

7. The method of claim 2, wherein the laser photons are free electron laser photons.

8. The method of claim 7, wherein the first source photon frequency is tuned by varying the electron energy.

9. The method of claim 7, wherein the first source photon frequency is tuned by varying the laser photon energy.

10. The method of claim 7, wherein the first source photon frequency is tuned by varying an angle of backscattering.

11. The method of claim 10, wherein the angle of backscattering is varied by collimation.

12. The method of claim 1, wherein the first source photons are coherent bremsstrahlung photons generated by passage of a beam of electrons through a periodic lattice.

13. The method of claim 12, wherein the first source photon frequency is tuned by varying the electron energy.

14. The method of claim 12, wherein the first source photon frequency is tuned by varying the periodic lattice.

15. The method of claim 12, wherein the first source photon frequency is tuned by varying an angle of the periodic lattice relative to the electron beam.

16. The method of claim 12, wherein the first source photon frequency is tuned by varying an angle of the periodic lattice relative to the bremsstrahlung photons.

17. The method of claim 1, wherein the first source photons are generated by a particle-induced reaction in a nucleus.

18. The method of claim 17, wherein the first source photon frequency is tuned by Compton scattering, of photons from the particle-induced reaction, by electrons.

19. The method of claim 17, wherein the first source photon frequency is tuned by varying an angle of the first source photons relative to a path of a particle inducing a reaction in the nucleus.

20. The method of claim 1, wherein the first source photons are generated by Compton scattering of photons by electrons.

21. The method of claim 20, wherein the first source photon frequency is tuned by varying an angle of Compton scattering.

22. The method of claim 1, wherein the overlap of the photon energy spectrum with the nuclear resonance is partial.

23. The method of claim 1, wherein the overlap of the photon energy spectrum with the nuclear resonance is total.

24. The method of claim 1, further comprising:
  A1) providing a second source of photons with a broad energy spectrum that overlaps a nuclear resonance in at least one nuclear species of interest;
  B1) prior to performing steps d) and e), illuminating the target sample with photons from the second source with the broad energy spectrum;
  C1) identifying a potential area in the target sample which may contain an item of interest upon an intensity of photons detected in at least one of the at least one detector energy channels of interest meeting a predetermined item of interest detection criterion; and
  D1) based upon the identification of the potential area, illuminating the potential area in the target sample with photons from the first source.

25. A method for detecting a potential item of interest in a target sample, the method comprising:
  a) providing a first source of photons, configured to generate photons by at least one of: Compton scattering of photons by electrons; passage of a beam of electrons through a periodic lattice; and a particle-induced reaction in a nucleus,
    wherein the first source photon frequency is tunable to a plurality of specific energies of interest;
  b) providing at least one reference scatterer, the reference scatterer comprising a plurality of nuclear species of interest;
  c) providing at least one photon detector to measure an intensity of photons scattered from the at least one reference scatterer in at least one energy channel;
  d) tuning the first photon source to a first specific energy of interest corresponding to a nuclear resonance in a nuclear species of interest;
  e) illuminating the target sample with photons from the first photon source having the first specific energy of interest;
  f) allowing photons from the first source transmitted through the target sample to scatter from the at least one reference scatterer;
  g) upon the intensity of photons detected in at least one of the at least one detector energy channels of interest meeting a predetermined first nuclear species of interest detection criterion, determining that the first nuclear species of interest has been detected;
  h). upon the intensity of photons detected in all energy channels of interest not meeting the predetermined first nuclear species of interest detection criterion, repeating steps e) to g) with the first photon source tuned to a further specific energy of interest corresponding to a nuclear resonance in a further nuclear species of interest.

26. The method of claim 25, wherein the first source photons are generated by backscattering of laser photons by energetic electrons.

27. The method of claim 26, wherein the first source photon frequency is tuned by varying the electron energy.

28. The method of claim 26, wherein the first source photon frequency is tuned by varying the laser photon energy.

29. The method of claim 26, wherein the first source photon frequency is tuned by varying an angle of backscattering.

30. The method of claim 29, wherein the angle of backscattering is varied by collimation.

31. The method of claim 26, wherein the laser photons are free electron laser photons.

32. The method of claim 31, wherein the first source photon frequency is tuned by varying the electron energy.

33. The method of claim 31, wherein the first source photon frequency is tuned by varying the laser photon energy.

34. The method of claim 31, wherein the first source photon frequency is tuned by varying an angle of backscattering.

35. The method of claim 34, wherein the angle of backscattering is varied by collimation.

36. The method of claim 25, wherein the first source photons are coherent bremsstrahlung photons generated by passage of a beam of electrons through a periodic lattice.

37. The method of claim 36, wherein the first source photon frequency is tuned by varying the electron energy.

38. The method of claim 36, wherein the first source photon frequency is tuned by varying the periodic lattice.

39. The method of claim 36, wherein the first source photon frequency is tuned by varying an angle of the periodic lattice relative to the electron beam.

40. The method of claim 36, wherein the first source photon frequency is tuned by varying an angle of the periodic lattice relative to the bremsstrahlung photons.

41. The method of claim 25, wherein the first source photons are generated by a particle-induced reaction in a nucleus.

42. The method of claim 41, wherein the first source photon frequency is tuned by Compton scattering, of photons from the particle-induced reaction, by electrons.

43. The method of claim 41, wherein the first source photon frequency is tuned by varying an angle of the first source photons relative to a path of a particle inducing a reaction in the nucleus.

44. The method of claim 25, wherein the first source photons are generated by Compton scattering of photons by electrons.

45. The method of claim 44, wherein the first source photon frequency is tuned by varying an angle of scattering.

46. The method of claim 25, wherein the overlap of the photon energy spectrum with the nuclear resonance is partial.

47. The method of claim 25, wherein the overlap of the photon energy spectrum with the nuclear resonance is total.

48. The method of claim 25, further comprising:
  A1) providing a second source of photons with a broad energy spectrum that overlaps a nuclear resonance in at least one nuclear species of interest;
  B1) prior to performing steps e), f) and g), illuminating the target sample with photons from the second source with the broad energy spectrum;
  C1) identifying a potential area in the target sample which may contain an item of interest upon an intensity of photons detected in at least one of the at least one detector energy channels of interest meeting a predetermined item of interest detection criterion; and
  D1) based upon the identification of the potential area, illuminating the potential area in the target sample with photons from the first source.

* * * * *